United States Patent [19]
Finnell et al.

[11] Patent Number: 5,830,168
[45] Date of Patent: Nov. 3, 1998

[54] ORTHOPEDIC HIP SUPPORT WITH MULTI-POSITIONAL JOINTS

[75] Inventors: Steven J. Finnell, Orlando; Bryan J. Puch, Apopka, both of Fla.

[73] Assignee: Orthomerica Products, Inc., Newport Beach, Calif.

[21] Appl. No.: 801,491

[22] Filed: Feb. 18, 1997

[51] Int. Cl.⁶ ........................................... A61F 5/00
[52] U.S. Cl. .................................. 602/24; 602/23
[58] Field of Search ................ 602/12, 16, 18–20, 602/23, 24; 24/31 V

[56] References Cited

U.S. PATENT DOCUMENTS

| | | | |
|---|---|---|---|
| 4,570,620 | 2/1986 | Kurtz et al. | 602/24 |
| 5,135,471 | 8/1992 | Houswerth | 602/19 |
| 5,470,310 | 11/1995 | Sutcliffe | 602/24 |
| 5,538,499 | 7/1996 | Schwenn et al. | 602/19 X |
| 5,676,642 | 10/1997 | Peters | 602/23 X |

*Primary Examiner*—Linda C. Dvorak
*Attorney, Agent, or Firm*—Price, Gess & Ubell

[57] ABSTRACT

An orthopedic hip support with multi-position joints for greater flexibility and comfort is disclosed. The hip support comprises left and right hip plates formed to mate with the hip region of the pelvis, a tightening belt and connecting front panel for adjusting the fit of the unit while supporting the abdomen, and a rear panel which connects the left and right hip plates therein forming the apparatus. Each hip plate is connected to the rear panel using a pin which permits relative rotation at the joint, and a preferred embodiment includes an elongated slot from which the pin can be positioned to expand or contract the apparatus. At mating surfaces of the rear panel and hip plates have abrasive, gritted surfaces which increase the friction between the two mating surfaces. When a compressive force is applied to the mating surfaces, such as a fastener with a wide head, the two surfaces can be securely positioned and the friction between the surfaces due to the abrasive surfaces resists slipping of the hip plates, allowing the hip plates to be positioned in a desired orientation and locked into position to provide a tailored, comfortable fit.

13 Claims, 3 Drawing Sheets

ORTHOPEDIC HIP SUPPORT WITH MULTI-POSITIONAL JOINTS

BACKGROUND OF THE INVENTION

1. Field of the Invention

The present invention relates to orthopedic supports, and more specifically to a novel hip support member having multi-positional expandable joints to accommodate various shapes and sizes of torsos more comfortably than those heretofore.

2. Description of Related Art

Hip stabilizing systems are well known in the orthopedic art and offer relief to a wide variety of people having different infirmities, such as those recovering from hip replacement surgery and other surgical procedures. A removable hip stabilizing system such as the present invention can in many cases permit ambulation to those users who might otherwise require a body cast. The purpose of the system is to secure the pelvis and protect the hip socket while permitting a limited range of motion of the thighs and legs. Hip stabilizing systems typically comprise two preformed shells or plates adapted to mate with the user's left and right hip, and a connector means for securing the plates in place comfortably and with the necessary pressure to allow the user to walk or sit without discomfort.

A difficulty with such a system lies in the varied sizes and shapes of the users of the device, and the need for the device to comfortably and effectively accommodate the various sizes and shapes. Males and females also have different shapes and require different attention in this area, making obvious the need for greater flexibility. First the shells or plates mating with the hips must be made to accommodate as many torso shapes as possible, although different models of the device can be created which vary in plate size or shape. Still, the securing of the plates with the proper pressure and at the desired angle remains a difficulty in the art to this day.

Modglin, U.S. Pat. No. 5,344,391 discloses a hip support which is designed to engage a patient's thigh and which is adjustable at front and rear portions. The Modglin reference teaches slidable guide means 10 for facilitating the proper positioning of the hip pads in which guide members slide laterally into and out of channels, but which provides no vertical adjustment. The absence of any vertical adjustment is recited to provide a more stable support, but comfort must be sacrificed in some cases where the hip plates must be angled individually with respect to a horizontal position. While Modglin provides a metal caliper at an intermediate position for adjusting the angle between the hip plates, individual control is not possible.

Mittasch, U.S. Pat. No. 3,548,817 discloses a brace which utilizes straps or belts to adjust the horizontal (i.e., circumferential) position and rods to set the vertical position of the brace. Although the upper portion of the brace may be expanded or contracted with relation to the lower portion, there appears to be no teaching of a brace that can pivot or be locked into a desired position. The use of straps may achieve a better fit, but only at the expense of rigidity because one can easily see that the Mittasch brace offers no resistance to collapse, only expansion.

Rolfes, U.S. Pat. No. 4,481,941 also teaches a hip brace which can be fitted by the use of straps or belts to tighten around a user's pelvis. Vertical stability is achieved by mounting the brace to a thigh support, and a locking connection can increase and decrease flexion depending on the selected screw position.

While each system described above enjoys some advantages, drawbacks exist in each system as to flexibility and support. The art is in need of a hip support which is multi-positional, capable of being locked in a desired position with an economy of parts. Each hip engaging member should be adjustable both angularly and horizontally to provide the greatest comfort and stability, and the adjustments should be individually independent to account for any asymmetry in the user's torso.

SUMMARY OF THE INVENTION

The above described deficiencies in the art are remedied by the present invention. The hip support of the present invention includes multi-positional joints which allow expansion of the support and rotation of the hip engaging plates independently from each other, thereby providing the greatest flexibility. Multi-positional slip resistant joints are formed by mating a textured or gritted surfaces (such as one would expect on a rough grade of sandpaper) which can be secured together and which resist sliding or rotation of the surfaces when an adequate pressure is applied. Pressure may be applied by a fastener at each joint, although other pressure means are envisionable. The support is placed loosely at first on the user and the desired position of the hip plates is determined. An adjustable belt is provided for providing general positioning and tightness of the support. When the position of the hip plates are finally established, including location and angular orientation, fasteners are tightened with the gritted surfaces of the hip plates and a connecting member meshing. Once tightened, the gritted surfaces resist motion because the friction between the surfaces due to the meshing abrasive surfaces is greater than most forces encountered which would tend to displace the support from its intended position, thereby providing a support which is both readily adjustable in angular orientation and expandable/contractible while being securely lockable in the desired position.

The objects and general purpose of the present invention are accomplished by an orthopedic hip support comprising first and second hip engaging plates, each having a designated area for connecting to a panel including holes for aligning with holes in the panel, where one of the aligned holes is elongated to provide for expansion of the connection. The panel and designated region have mating surfaces when a fastener is disposed within the aligned holes, and the mating surfaces are covered with an abrasive, textured surface which increases the coefficient of friction between the mated surfaces. The increase in the friction resists relative motion between the panel and the hip plate when the fastener is securely tightened, thereby providing a substantially rigid support which is extremely flexible, easy to manipulate, inexpensive to manufacture, and cost effective. The hip support of the present invention also addresses the problem of an orthoses edema.

BRIEF DESCRIPTION OF THE DRAWINGS

The exact nature of this invention, as well as its objects and advantages, will become readily apparent upon reference to the following detailed description when considered in conjunction with the accompanying drawings, in which like reference numerals designate like components throughout the figures thereof, and wherein.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide a hip support apparatus with multi-positional slip resistant joints.

Figure 1:
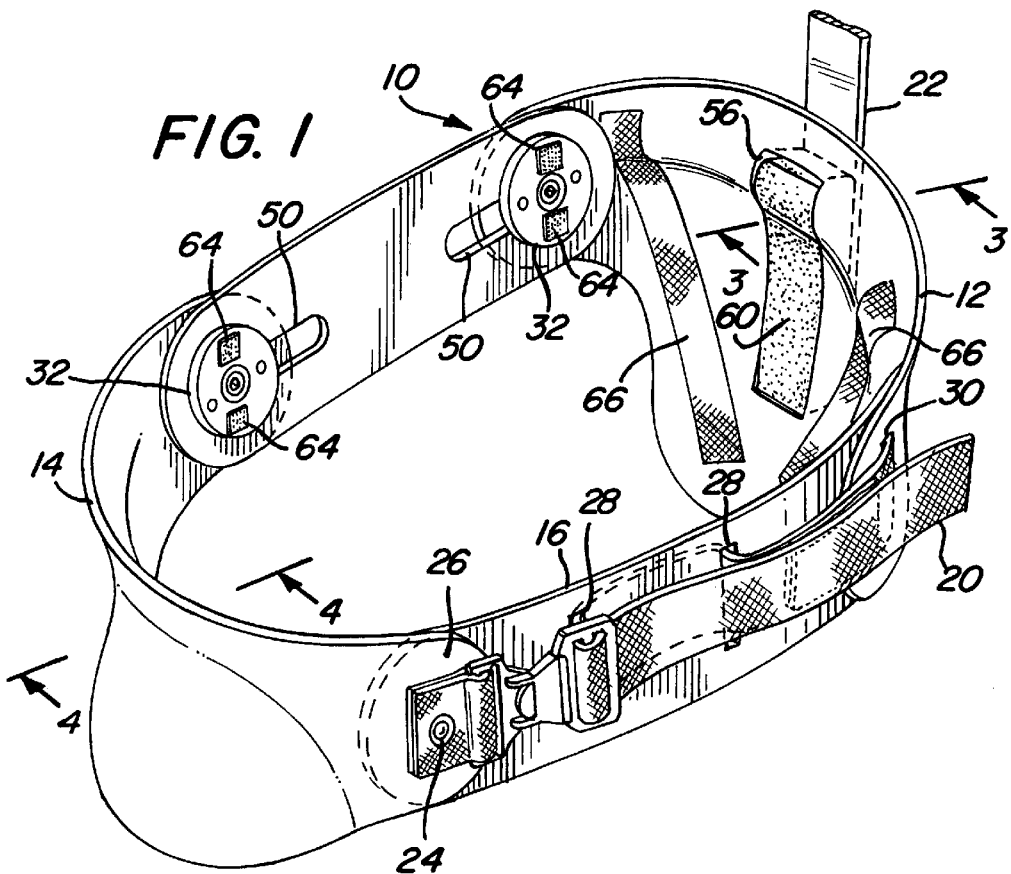
FIG. 1 is an elevated view of the orthopedic hip support of the present invention.

A preferred embodiment 10 of present invention is illustrated generally in FIG. 1, which shows an orthopedic hip support having a first hip plate 12, a second hip plate 14, a generally flexible front stabilizer 16 with a belt 20 for tightening the unit, and a rear connector panel 18 which is used to secure the unit from the rear. Each hip plate is pre-formed of a substantially rigid material, preferably a plastic such as high density polyethylene, which can be heat-molded into a shape which conforms to the contours of an average human hip. It is to be understood that the size and shape of the hip plates can be altered without deviating from the scope of the present invention, and the given shapes are for illustrative purposes only. One hip plate 12 may be longer than its paired hip plate 14 if an extension member 22 is to be attached, as shown in FIG. 1. It is often times necessary to support another part of the body, such as an arm cast, by propping the cast against the hip plate 12. It may also be advantageous to connect the brace to a lower part of the body, such as the thigh. Because of the need to coordinate the hip support with other brace apparatus, it is critical that the hip plate 12 be located so as to align the mounting bracket (not shown) vertically and at the location of the hip most comfortably able to bear the additional load. Enlarging the hip plate distributes the load over a larger area which can alleviate localized stresses and is consequently more comfortable to the patient.

One hip plate 14 is shown having a rivet 24 which secures a belt 20 at the front edge 26 of the hip plate 14. The belt 20 passes through two slots 28 in the front stabilizer 16 and through a slot 30 in the other hip plate 12 in such a manner as to draw the two hip plates 12, 14 closer together as the belt 20 is tightened and expands the support as the belt 20 is loosened. The front stabilizer 16 supports the abdomen and disperses the forces produced by the belt, and is generally a resiliently flexible material such as a plastic which is easy to shape and manufacture.

Figure 2:
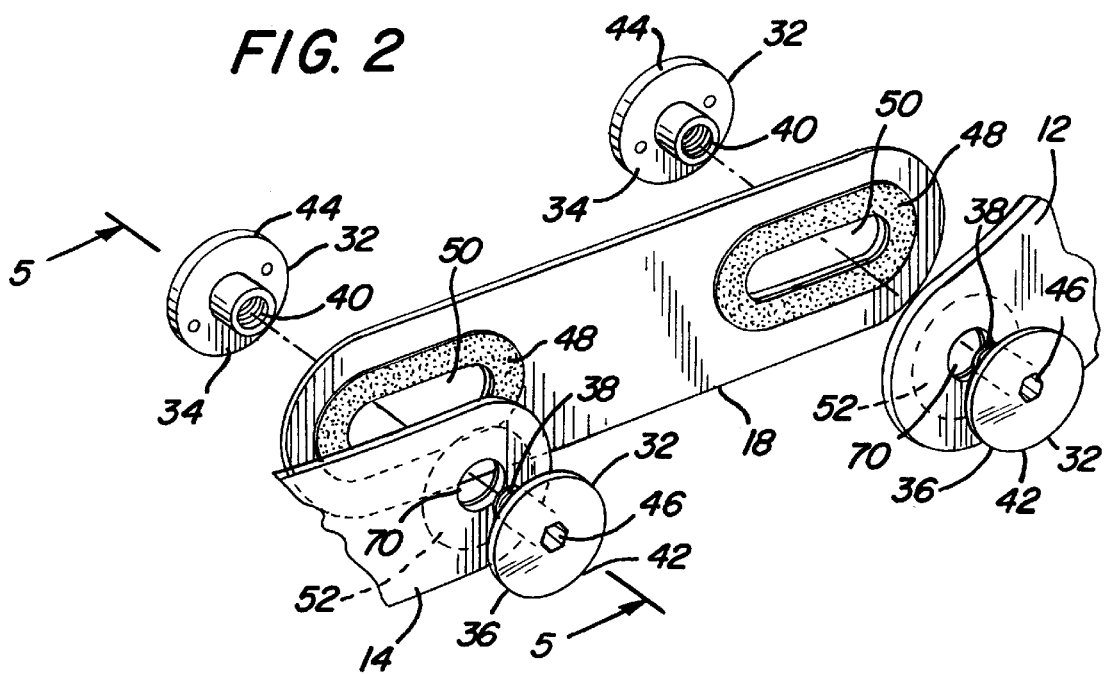
FIG. 2 is an exploded view of the joints of the hip support of FIG. 1.

Each hip plate 12, 14 is connected to the rear panel 18 by a fastener 32 as shown in FIG. 2. Holes or apertures 70 in the hip plates 12, 14 are aligned with holes 50 in the connector panel 18, and a pin or fastener 32 is inserted into the holes will preferably be of the type wherein a male component 36 with outer threads 38 is insertable into a female component 34 having a tapped hole 40, where both the male and female components have relatively large flattened heads 42, 44. The size of the heads of the fasteners increase the area influenced by the fasteners, and as a consequence increases the effectiveness of the joint's slip resistant characteristics. In FIG. 2, the heads of the fasteners are shown to slightly overlap the edge of the abrasive surfaces, described more fully below. A flatter head is preferably because it is less obtrusive and more comfortable than a head which protrudes significantly. As the male component 36 is rotated, the fastener 32 contracts until a compressive force between the two heads 42, 44 is achieved. A hexagonal hole 46 is provided for insertion of a tool (not shown) into one or both of the components to tighten and release the fasteners, thus providing a releasable method for applying a compressive force to the mating surfaces of the hip plates and the rear connector panel 18.

Figure 3:
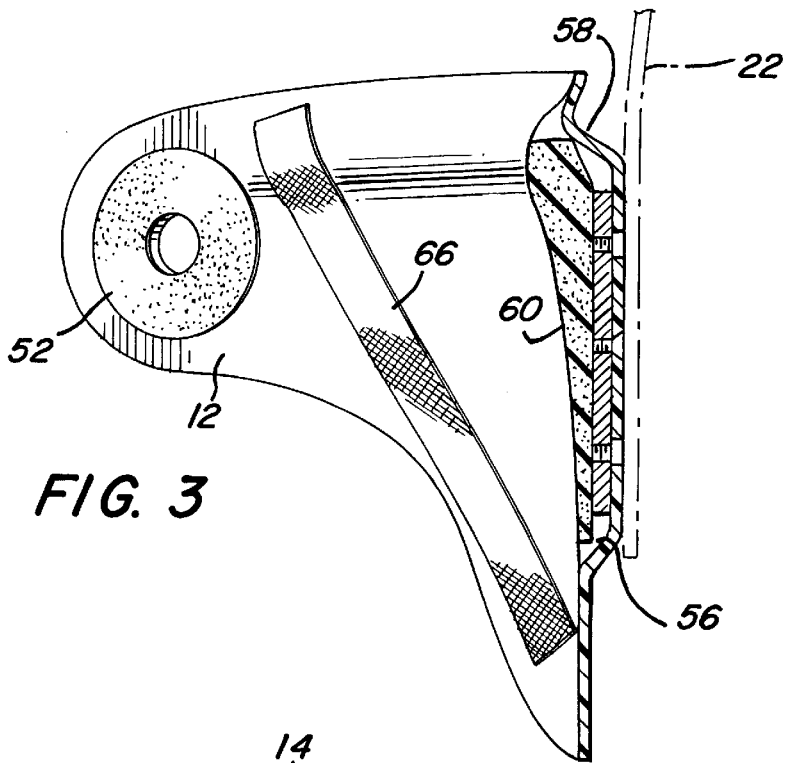
FIG. 3 is a front view of the gritted region of the first hip engaging plate and a cross sectional view of the pad and the vertical column.
Figure 4:
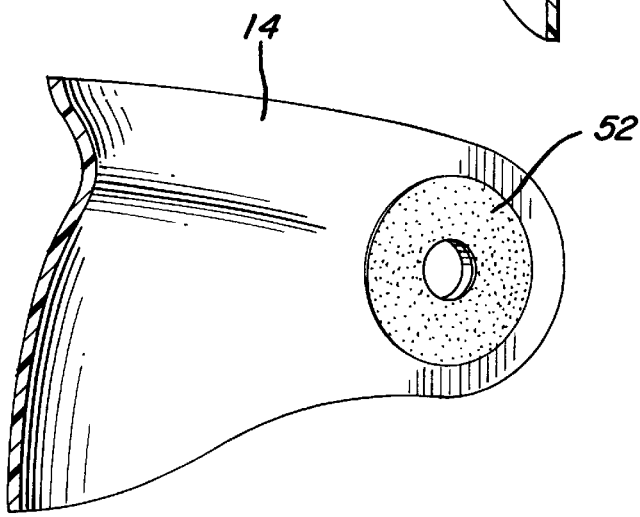
FIG. 4 is a front view of the gritted region of the other hip engaging plate.

FIGS. 2 through 4 illustrate an abrasive or gritted surfaces 48, 52 around the holes in the rear connector panel 18 and the hip engaging plates 12, 14. The gritted surfaces 48, 52 have a rough sandpaper texture which are designed to withstand rubbing without diminishing its texture, and is achieved either by processing the surface of the hip plate to achieve the desired texture or by affixing a sheet or other element to the surface of the hip plate by adhesive or other commercially viable means. The gritted surfaces mate with the connecting surface so that there is a texture on texture interface between the two connected pieces. The two abrasive surfaces cooperate to resist slip between the two pieces when the fasteners 32 are tightened because the friction required to overcome the two meshing abrasive surfaces is more than is typically encountered during normal operation of a brace of this kind. Although the dimensions of the friction enhancing surface may vary, a typical area will comprise a three quarters of an inch to one inch wide strip of textured surface around each of the respective holes. The fastener heads would typically just extend beyond the textured surface, having diameters of one and one half inches to two inches. The size of the frictional surfaces and the fasteners can be varied depending on the size of the user and the forces which may be anticipated to be encountered by the joint.

When the hip support 10 is initially placed on the user, the fasteners 32 are loosened to provide free movement of the hip plates 12, 14 with respect to the connector panel 18. As can be appreciated, the hip plates swivel or rotate about the fasteners, providing a free range of rotation for each hip plate to move independent of the other hip plate. The hip plates are positioned first by placing each plate on its respective hip, and then the belt may be tightened to obtain a first fit. Once the hip plates are in the properly rotated and mounted position, the fasteners 32 are tightened producing a compressive force on the joints which "lock" the joints in place without the need for incremental settings. A tool such as an allen wrench (not shown) may be provided to tighten the fasteners by insertion into the hole 46. When each fastener is sufficiently tightened, the hip support 10 will remain in its intended position without requiring readjustment, and the hip support can be removed by unbuckling the belt 20 while the hip plates 12, 14 remain properly mounted.

As a further adjustment, the holes 50 in the rear connector panel 18 or the hip plates may be oblong so that the hip plate can be both rotated and moved laterally for even greater individual tailoring. The hip plate is moved along the oblong slot 50, which is preferably orientated such that its major axis is in the circumferential direction with respect to the torso of the user. This will allow users of varying girth to wear the hip support 10 comfortably and safely. As shown in FIG. 2, an oblong hole 50 will have a similar oblong abrasive pattern 48 around it to mesh with the frictionally enhanced surface of the hip plate to resist sliding.

Additionally, the abrasive surface of the hip plate 52, seen in FIGS. 3 and 4, are preferably of a similar roughness to that of the connector panel 18 to prevent one surface from prematurely wearing off.

Figure 5:
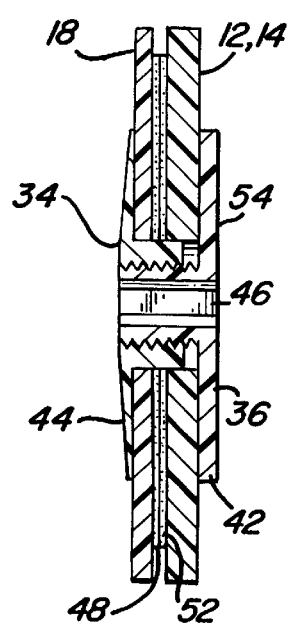
FIG. 5 is a cross-sectional view of the joint of FIG. 2.

FIG. 5 illustrates a preferred embodiment of the joint 54 of the present invention in cross section. Hip plate 12, 14 and connector panel 18 are compressed together with mating abrasive surfaces 48, 52 in contact to increase the friction between the two surfaces. A fastener comprising a male component 36 and a female component 34 compresses the joint 54 using traditional mechanics, while enlarged heads 42, 44 on the male and female components provide an enlarged compression area between the heads, which increases the frictional forces between the two elements. Once the fastener is sufficiently tightened, the joint 54 will resist slip between the two elements providing a releasable but lockable multi-position joint.

Another feature of the present invention relates to the development of a phenomenon known as window edema, which tends to develop adjacent discontinuities in a hip support. Window edema occurs when the body begins to fill a crevass or channel in part due to the pressure applied by the support. Hip plate 12 is shown having an inner channel 56 formed as a result of outer column 58 which is adapted to mount extension member 22. To deter the formation of window edema in inner channel 56, a pad 60 is placed inside the inner channel significantly reducing the occurrence of window edema.

Figure 6:
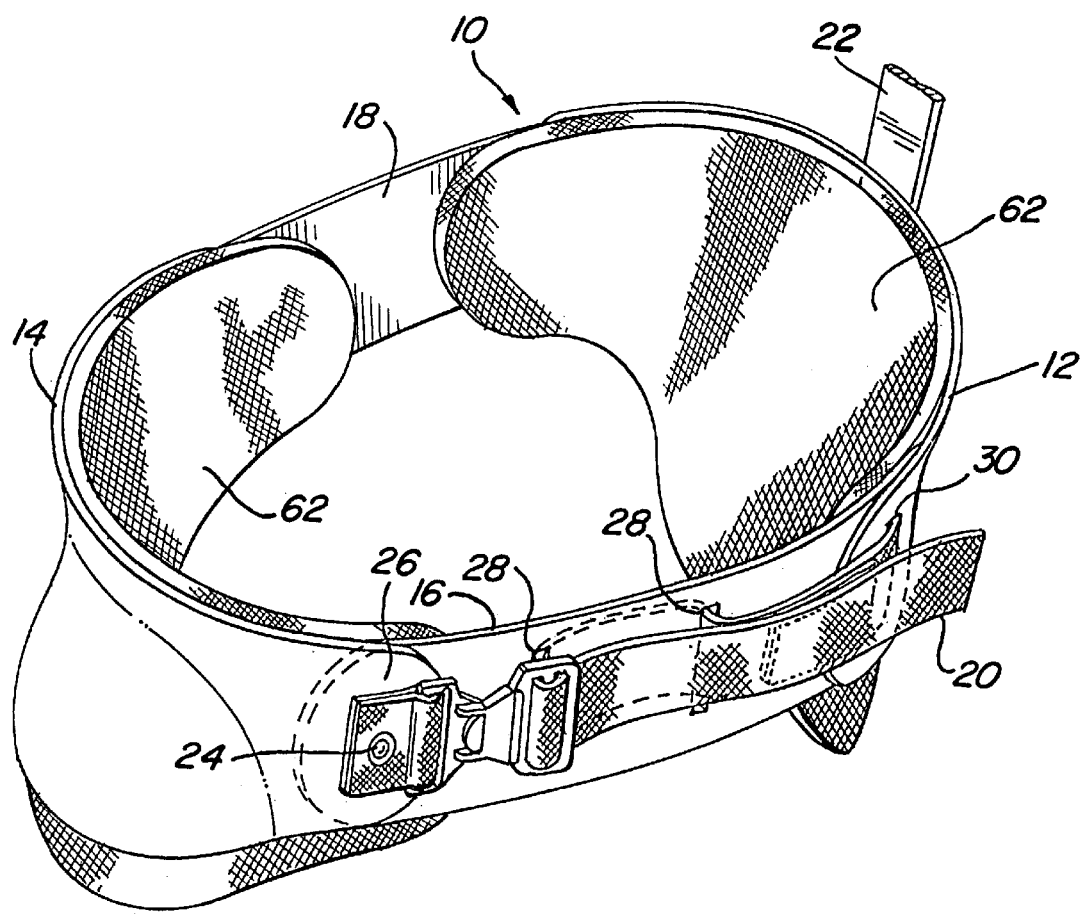
FIG. 6 is an elevated view of the hip support with flexible pads attached.

FIG. 6 illustrates a preferred embodiment of the present invention with flexible cushions or pads 62 placed adjacent each hip plate. These cushions are preferably removably secured to the hip support using strategically located patches of a hooks and loops fastening system such as VELCRO®. For example, FIG. 1 illustrates each fastener 32 including VELCRO® patches 64 which cooperate with either the fabric of the cushions 62 or additional patches (not shown) on the cushions 62. Moreover, strips of VELCRO® 66 may preferably be provided on each hip plate to retain the cushions 62.

It will be understood that the embodiments described herein are merely exemplary and that a person skilled in the art may make many variations and modifications without departing from the spirit and scope of the invention. All such variations and modifications are intended to be included within the scope of the invention as defined in the appended claims.

What is claimed is:

1. A slip resistant multi-positional joint for use with an orthopedic support comprising:
   first and second elements of the orthopedic support adapted to be releasably fastened together along continuous radial orientations about a pin, said first element comprising a gritted frictionally enhanced surface, said second element comprising a gritted frictionally enhanced surface mating with said gritted frictionally enhanced surface of said first element; and
   means cooperating with said pin for releasably applying a compressive force to said first and second elements at said gritted frictionally enhanced surfaces whereby the friction between the gritted frictionally enhanced surfaces due to said compressive force is sufficient to resist slip between said first and second elements.

2. A multi-positional hip support comprising:
   first and second hip engaging members each having an aperture therethrough, each said hip engaging member further comprising a gritted frictionally enhanced surface about the aperture;
   a connector member having first and second ends each adapted to mount to one of said hip engaging members, said first and second ends each comprising a hole therein and a gritted frictionally enhanced surface about the hole, each hole operably aligned with the aperture of one of said first and second hip engaging members such that the gritted frictionally enhanced surface about the aperture cooperates with the gritted frictionally enhanced surface about the hole to resist rotation of said connector with respect to said hip engaging members when a compressive force is applied to said gritted frictionally enhanced surfaces;
   fastener means cooperating with said apertures and said holes for releasably applying a compressive force to said gritted frictionally enhanced surfaces; and
   means for securing said hip engaging members and said connector to a torso.

3. The multi-positional hip support as recited in claim 2 wherein said holes in said first and second ends of said connector are oblong with an elongated axis in a circumferential direction with respect to said torso thereby allowing expansion and contraction of said hip support, said gritted frictionally enhanced surfaces further cooperating to resist sliding of said connector and said hip engaging members when said compressive force is applied to said gritted frictionally enhanced surfaces.

4. The multi-positional hip support as recited in claim 2 wherein one of said first and second hip engaging members further comprises a protruding column formed on an outer surface thereof adapted for mounting an extension member thereto, said protruding column coincidentally forming an inner channel on the inner surface of said hip engaging member, said multi-positional hip support further comprising pad means substantially filling said inner channel for discouraging the development of window edema.

5. A slip resistant multi-positional joint for use with an orthopedic support comprising:
   first and second elements of the orthopedic support adapted to be releasably locked together in multiple positions and orientations, said first element comprising an aperture therein and a gritted frictionally enhanced surface about said aperture, and said second element comprising a hole aligned with the aperture of said first element and gritted frictionally enhanced surface means about said hole for resisting slip between said first and second elements when a compressive force is applied to said first and second elements; and
   fastener means passing through said aperture and said hole for applying the compressive force to said first and second elements.

6. The slip resistant multi-positional joint as recited in claim 5 wherein said aperture is oblong in shape, and said fastener means sets an orientation and position of said second element along said aperture.

7. The slip resistant multi-positional joint as recited in claim 6 wherein said fastener means comprises a male component having an enlarged generally flattened head and an externally threaded shaft, and a female component having an enlarged generally flattened head and a shaft including a tapped hole therein sized to receive said threaded shaft, said male component and said female component cooperating to produce a compressive force when a rotation of one component is applied with respect to a second component.

8. An orthopedic hip support having multi-position joints adapted for fixing adjacent connecting components in any radial position comprising:
   a first hip engaging member formed to conform to the contour of a human hip, said first hip engaging member comprising a substantially rigid plate having a hole therein located generally on a rearward half thereof, and further comprising an abrasive patch about said hole on a surface of said first hip engaging member for frictionally resisting slip between said first hip engaging member and an abutting surface thereto;

a second hip engaging member formed to conform to the contour of a human hip, said second hip engaging member comprising a substantially rigid plate having a hole therein located generally on a rearward half thereof, and further comprising an abrasive patch about said hole on a surface of said second hip engaging member for frictionally resisting slip between said second hip engaging member and an abutting surface thereto;

belt means connectable to said first and second hip engaging members at generally forward halves thereof for fastening said first and second hip engaging members to a user;

connector member mountable to said first and second hip engaging members at said respective holes, said connector member including first and second pin means insertable in said holes for rotatably mounting said first and second hip engaging members thereto such that said first and second hip engaging members swivel about one of said pin means, each said pin means further comprising means for releasably compressing said connector member to one of said first and second hip engaging members at said abrasive patches to fix a relative position of said connector member and said hip engaging member.

9. The orthopedic hip support as recited in claim 8 wherein said abrasive patch for frictionally resisting slip between said first hip engaging member and an abutting surface comprises a sheet of material having an abrasive surface on a first side, and a second side adhesively affixed to said hip engaging member.

10. The orthopedic hip support as recited in claim 9 wherein said connector means further comprises an abrasive surface disposed about said pin means to mate with said abrasive patches of said hip engaging members to resist slip between said hip engaging members and said connector.

11. The orthopedic hip support as recited in claim 8 wherein said first hip engaging member comprises a column formed along an exterior surface thereof adapted to mount an extension thereto, said column forming a corresponding channel at an inner surface of said first hip engaging member, and wherein said orthopedic hip support further comprises pad means substantially filling said channel for reducing the occurrence of window edema.

12. The orthopedic hip support as recited in claim 8 further comprising flexible pads mounted to said first and second hip engaging members generally at an inner surface thereof, and means for releasably securing said flexible pads to said first and second hip engaging members.

13. An expandable, multi-positional hip support comprising:

left and right hip engaging plates;

a belt connecting a front portion of said left and right hip engaging plates;

a rear connector member connected to a rear portion of said left and right hip engaging plates, said rear connector member comprising left and right slots where said rear portions of said left and right hip engaging plates are selectively positioned there within to selectively adjust said hip support;

an abrasive, gritted region on mating surfaces of said left hip engaging plate and said rear connector member, and also on said right hip engaging plate and said rear connector member; and a compressing member disposed in said left slot compressing said abrasive gritted region on said left hip engaging plate with the associated abrasive, gritted region on said rear connector member, and a compressing member disposed in said right slot compressing said abrasive gritted regions on said right hip engaging plate with the associated abrasive, gritted region on said rear connector member, said compressing members cooperating to fix the position of said left and right hip engaging plates.

* * * * *